(12) United States Patent
Narasimhan et al.

(10) Patent No.: US 6,315,989 B1
(45) Date of Patent: Nov. 13, 2001

(54) WATER IN OIL MICROEMULSION PEROXIDE COMPOSITIONS FOR USE IN COLORING HAIR AND RELATED METHODS

(75) Inventors: Saroja Narasimhan, Matawan; Alexander C. Chan, Cranbury; Dalal Ibrahim Duffer, North Brunswick, all of NJ (US); Geoffrey Robert Hawkins, Langhorne, PA (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/470,392

(22) Filed: Dec. 22, 1999

(51) Int. Cl.$^7$ .............. A61K 7/135; A61K 7/06
(52) U.S. Cl. ............ 424/62; 424/70.1; 424/70.19; 424/70.21; 424/70.22; 424/70.27; 424/70.31; 8/405; 8/406
(58) Field of Search ............. 424/70.1, 70.19, 424/70.21, 70.22, 70.24, 70.27, 70.31, 62; 8/405, 406

(56) References Cited

U.S. PATENT DOCUMENTS

| | | | |
|---|---|---|---|
| 4,146,499 | * | 3/1979 | Rosano . |
| 4,472,291 | * | 9/1984 | Rosano . |
| 4,560,554 | | 12/1985 | Kubo ................ 424/71 |
| 4,784,801 | | 11/1988 | Hoeffkes ............ 252/554 |
| 4,976,742 | | 12/1990 | Rose ................. 8/412 |
| 4,994,087 | | 2/1991 | Konrad .............. 8/409 |
| 4,997,451 | | 3/1991 | Clausen ............. 8/421 |
| 5,102,655 | | 4/1992 | Yoshihara .......... 424/62 |
| 5,587,155 | | 12/1996 | Ochiai .............. 424/70.28 |
| 5,589,177 | | 12/1996 | Herb ................. 424/401 |
| 5,597,792 | | 1/1997 | Klier ................. 510/417 |
| 5,641,480 | | 6/1997 | Vermeer ............. 424/70.24 |
| 5,656,280 | | 8/1997 | Herb ................. 424/401 |
| 5,658,575 | | 8/1997 | Ribier ............... 424/401 |
| 5,688,930 | | 11/1997 | Bertho ............... 536/18.6 |
| 5,696,074 | | 12/1997 | Nickel ............... 510/470 |
| 5,785,961 | | 7/1998 | Nakama ............. 424/70.19 |

* cited by examiner

Primary Examiner—Thurman K. Page
Assistant Examiner—Brian K. Seidleck
(74) Attorney, Agent, or Firm—Julie Blackburn

(57) ABSTRACT

A water in oil microemulsion peroxide composition for coloring or lightening of hair comprising 1–99% of an aqueous phase in the form of dispersed microdroplets having a droplet size of 100 to 1500 Angstroms, 0.1–75% of a continuous oil phase; and 1–65% of an organic, surface active ingredient capable of interacting with the water phase and the oil phase to cause formation of the dispersed aqueous phase microdroplets, all percentages by weight of the total composition; and a method for coloring or lightening hair using the peroxide composition, and a method for reducing the amount of time necessary to permanently color hair using the peroxide composition.

20 Claims, No Drawings

WATER IN OIL MICROEMULSION PEROXIDE COMPOSITIONS FOR USE IN COLORING HAIR AND RELATED METHODS

TECHNICAL FIELD

The invention is in the field of peroxide compositions for use in lightening or coloring hair, and methods for lightening or coloring hair using the composition.

BACKGROUND OF THE INVENTION

A large majority of women color their hair, either to cover gray or permanently change hair color. Permanent change in hair color may be obtained by oxidative dyes or bleaching. Oxidative hair dyes are widely used since they provide permanent color to hair, generally lasting from four to six weeks. Oxidative hair dyes are usually sold in the form of a two component kit. In one container is an aqueous alkaline composition in the liquid or creme form that contains oxidative colorant precursors in addition to other ingredients. In the other container is a developer solution that contains an oxidizing agent, usually hydrogen peroxide. The two components are mixed immediately prior to use and applied to hair. The dye precursors in the lotion then penetrate the hair, and the oxidizing agent oxidizes the dye precursors to produce color in the hair, as well as lightening the melanin in the hair. The mixture is left on the hair for an appropriate period of time, generally 20 to 60 minutes, then rinsed off with water.

Most consumers complain that a hair color process that takes 20 to 60 minutes is too long. It is estimated that if oxidative dyeing and bleaching of hair were a 5 to 10 minute process, more consumers would be inclined to color their hair. Certain commercial products exist that advertise 5 to 10 minute color, but these systems are not capable of permanently lightening hair, or causing a permanent color change to hair. Thus, the current commercial products have limited usefulness.

Accordingly, there is a need for providing compositions and processes for oxidative dyeing and/or bleaching of hair that enables permanent coloration of hair in 5 to 10 minutes. The coloring will include covering gray as well as providing permanent color change to the hair.

Microemulsions are used in cosmetics such as skin care emulsions, hair care products and the like. Microemulsions refer to oil in water, or water in oil, emulsions where the dispersed phase droplets are of a much smaller size than usual, e.g. submicron size. Thus the name, microemulsion.

It has most unexpectedly been discovered that when peroxide compositions used in bleaching or oxidative dyeing of hair are in the form of water in oil microemulsions, the amount of time necessary to color the hair is substantially reduced.

It is an object of the invention to provide a peroxide composition in the microemulsion form, in particular a water in oil microemulsion, for use in bleaching or oxidative dyeing of hair.

It is another object of the invention to provide a peroxide composition for use in a five to ten minute process for bleaching or oxidative dyeing of hair.

It is another object of the invention to provide a method for oxidative dyeing and/or bleaching of hair in five to ten minutes.

It is another object of the invention to provide an oxidative hair dye or bleach composition, mixed immediately prior to use, that is in the microemulsion form.

It is another object of the invention to provide a method for reducing the amount of time necessary to permanently lighten and/or color hair (usually about 20 to 60 minutes) by using peroxide compositions in the microemulsion form.

It is another object of the invention to provide a method for permanently lightening and/or coloring hair with a microemulsion composition comprised of a mixture of peroxide composition in the water in oil microemulsion form, and an alkaline composition, wherein the presence of dispersed microdroplets facilitates the increased penetration of the active ingredients into the hair shaft, and thereby reduces the amount of time necessary to achieve lightening or permanent coloration of the hair.

It is another object of the invention to provide a method for oxidative dyeing of hair with a water in oil microemulsion composition comprised of a mixture of water in oil microemulsion peroxide and oxidative hair dye, wherein the presence of the dispersed microdroplets causes increased penetration of the active ingredients, e.g. the oxidative dye intermediates and the oxidizing agent, into the hair shaft, and thereby decreasing the amount of time necessary to achieve full coloration of the hair.

SUMMARY OF THE INVENTION

The invention comprises a water in oil microemulsion peroxide composition for coloring or lightening hair comprising:
 (a) 1–99% of an aqueous phase in the form of dispersed microdroplets having a droplet size of 100 to 1500 Angstroms,
 (b) 0.1–75% of a continuous oil phase; and
 (c) 1–65% of an organic, surface active ingredient capable of interacting with the water phase and the oil phase to cause formation of the dispersed aqueous phase microdroplets, all percentages by weight of the total composition.

The invention also comprises a method for coloring or lightening hair comprising the steps of:
 (a) combining, immediately prior to use,
  (1) an aqueous alkaline composition comprising at least one interactive surfactant; and
  (2) a peroxide composition for coloring or lightening hair comprising, by weight of the total composition:
   (a) 1–99% of an aqueous phase in the form of dispersed microdroplets having a droplet size of 100 to 1500 Angstroms,
   (b) 0.1–75% of a continuous oil phase; and
   (c) 1–65% of an organic, surface active ingredient capable of interacting with the water phase and the oil phase to cause formation of the dispersed aqueous phase microdroplets, all percentages by weight of the total composition.
 (b) applying said mixture of (1) and (2) to the hair to cause coloration of the hair.

The invention further comprises a method for reducing the amount of time required to permanently color hair, comprising treating the hair with a mixture of a water in oil microemulsion peroxide composition and an oxidative dye composition containing an interactive surfactant.

DETAILED DESCRIPTION

All percentages mentioned herein are percentages by weight unless otherwise indicated. The compositions and methods of the invention are capable of coloring or lightening hair or both.

I. THE PEROXIDE COMPOSITION

The peroxide composition comprises a water phase, an oil phase, and an organic, surface active ingredient capable of interacting with the water phase and the oil phase to cause formation of dispersed aqueous phase microdroplets having a droplet size of 100 to 1500 Angstroms.

A. The Aqueous Phase

The composition of the invention comprises 1–99%, preferably, 5–65%, more preferably 10–50% by weight of the total peroxide composition of an aqueous phase in the form of dispersed microdroplets having a droplet size of 100 to 1500 Angstroms, preferably 200 to 1000 Angstroms, more preferably 250 to 700 Angstroms. The aqueous phase contains water and hydrogen peroxide, and, preferably, one or more penetration enhancers, in addition to other desirable water soluble polar ingredients. A variety of ingredients are suitable for use in the aqueous phase provided such ingredients are water soluble.

1. Water

The peroxide composition comprises, by total weight of the peroxide composition, about 1–55%, preferably 1–50%, more preferably 1–45% water.

2. Hydrogen Peroxide

The peroxide composition further comprises about 1–45%, preferably 1–40%, more preferably 1–35% by weight of the total peroxide composition of hydrogen peroxide.

3. Penetration Enhancers

The peroxide composition preferably comprises, 0.1–55%, preferably 0.5–50%, more preferably 1–45% by weight of the total peroxide composition of a penetration enhancer, which is an ingredient which is soluble in the aqueous phase and interacts with the other aqueous phase ingredients to enhance penetration of the hydrogen peroxide into the hair shaft, usually by softening the hair fiber and exerting a plasticizing effect. Particularly preferred penetration enhancers are dihydric, or polyhydric alcohols, as well as sugars and other types of humectants. Suitable sugars include glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like. Preferred is where the penetration enhancer is ethoxydiglycol.

4. Monohydric Alcohols

Preferably, the compositions of the invention comprise 0.1–40%, preferably 1–35%, more preferably 2–30% of one or more mononhydric alcohols. Suitable monohydric alcohols include ethanol, isopropanol, benzyl alcohol, butanol, pentanol, ethoxyethanol, and the like. The monohydric alcohols interact with the surfactant to facilitate formation of the microemulsion.

5. Other Ingredients

The water phase of the peroxide composition may additionally comprise one or more water soluble, polar ingredients that are compatible in the aqueous phase including water soluble colorants, preservatives, plant extracts, and the like.

B. The Oil Phase

The peroxide compositions of the invention comprise 0.1–60%, preferably 0.5–50%, more preferably 1–45% by weight of a continuous oil phase. The term "continuous" means that the oil phase forms the continuous phase of the emulsion. The term "oil phase" means at least one lipophilic ingredients that, either alone or in combination with other lipophilic ingredients, forms a liquid phase at room temperature, said liquid phase not being miscible with the water phase in the absence of the organic surface active agent. The oil may be a volatile oil or a nonvolatile oil. The term "volatile" means an oil having a vapor pressure of 2 mm. of mercury or greater at 20° C. The term "nonvolatile" means an oil having a vapor pressure of less than 2 mm. of mercury at 20° C.

1. Volatile Oils

Suitable volatile oils for use in the composition include volatile paraffinic hydrocarbons having a viscosity of 0.5 to 10 centipoise at 25° C.

(a) Volatile Hydrocarbons

Examples of volatile hydrocarbons include various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818, 105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISO-PARS trademark, and from the Permethyl Corporation. Suitable $C_{12}$ isoparaffins, e.g. isododecane, are manufactured by Permethyl Corporation under the tradename Permethyl 99A. Various $C_{16}$ isoparaffins commercially available, such as isohexadecane (having the tradename Permethyl R), are also suitable.

2. Nonvolatile Oils

A variety of nonvolatile oils are suitable for use in the compositions, including various nonvolatile organic oils. Suitable nonvolatile oils preferably have a viscosity of 10 to 1,000,000, preferably 20–500,000 centipoise at 25° C.

(a) Nonvolatile Organic Oils (i) Esters

Examples of nonvolatile oils suitable for use in the compositions of the invention include esters formed by the reaction of a carboxylic acid-containing compound with an aliphatic or aromatic alcohol. Preferably, such esters have the general formula RCO-OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isopropyl myristate, isotridecyl isononanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 1558–1565 of the *C.T.F.A. International Cosmetic Ingredient Dictionary and Handbook*, Seventh Edition, 1997, which is hereby incorporated by reference.

Other esters include glyceryl esters of fatty acids, or triglycerides. Both vegetable and animal sources may be used. Examples of such oils include castor oil, lanolin oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

(ii) Hydrocarbons

Also suitable as the oil are nonvolatile hydrocarbons such as isoparaffins, hydrogenated polyisobutene, mineral oil, squalene, petrolatum, and so on.

(iii) Fatty Alcohols

Straight or branched chain fatty alcohols that are liquids at room temperature, having the formula R—OR wherein R is a straight or branched chain saturated or unsaturated alkyl having 6–30 carbon atoms, are also suitable oils. Such fatty alcohols include cetyl alcohol, cetearyl alcohol, and the like.

(iv) Lanolin and Dervatives Thereof

Also suitable as the oil are various lanolin derivatives such as acetylated lanolin, acetylated lanolin alcohol, and so on.

In the preferred embodiment of the invention, the oil component comprises one or more nonvolatile organic oils which are esters, most particularly esters formed by the reaction of a short chain alcohol such as ethanol, isopropanol, and the like with a fatty acid having 10–22 carbon atoms. Most preferred is isopropyl myristate.

3. Other Ingredients

The peroxide composition may contain one or more additional ingredients that form part of the oil phase, provided those ingredients are lipophilic in character and are miscible with the other oil phase ingredients. Examples of such materials include waxes, preservatives, fragrance oils, and the like.

C. Surface Active Ingredient

The peroxide composition of the invention comprises 1–65%, preferably 3–60%, more preferably 5–55% by weight of an organic, surface active ingredient that is capable of interacting with the aqueous phase and the oil phase to cause formation of aqueous phase microdroplets having a droplet size of 100 to 1500 Angstroms which are dispersed in the continuous oil phase. Preferably, the surface active ingredient contains both lipophilic and hydrophilic portions such that the hydrophilic portion of the molecule is attracted to, and orients with, the polar, aqueous phase ingredients in the composition, and the lipophilic portion of the molecule is attracted to, and orients with the nonpolar, oil phase of the peroxide composition. Examples of radicals that will confer hydrophilicity include hydroxypolyethyleneoxy, hydroxy carboxylates, sulfonates, sulfates, phosphates, or amines. Examples of radicals that will confer lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interrupted by one or more oxygen atoms, a benzene ring, amides, esters, or other functional groups. Examples of suitable organic, amphiphilic, surface active agents include nonionic, amphoteric, cationic, and anionic surface active agents. The organic, amphiphilic, surface active agent may be a liquid, semi-solid, or solid at room temperature.

1. Nonionic Surface Active Agents

A variety of nonionic surface active agents are suitable for use as the organic, amphiphilic, surface active agents. Preferably, the nonionic surface active agents have an HLB (hydrophile/lipophile balance) of 12–20, more preferably 13–16. Examples of nonionic surfactants include:

(a) Alkoxylated Alcohols

Suitable alkoxylated alcohols include ethers formed from the reaction of an aliphatic, aromatic, or heterocyclic alcohol with an alkylene oxide, generally ethylene or propylene oxide. Preferably, the alcohol is an aliphatic alcohol, more preferably a fatty alcohol having 10–22 carbon atoms; and the alkylene oxide is ethylene oxide. Examples of preferred alkoxylated alcohols include steareth, ceteth, ceteareth, beheneth, and the like, having from 1 to 200 repeating ethylene oxide units, as well as PEG derivatives of fatty acids such as PEG dioleate, PEG distearate, PEG isostearate, and so on.

(b) Sorbitan Derivatives

Suitable sorbitan derivatives are esters or ethers or sorbitan, which is a heterocyclic ether formed by the dehydration of sorbitol. Sorbitan may be derivatized by ethoxylation and/or esterification of the hydroxyl groups. Suitable acids used for esterification include C1–30 acids, more preferably, fatty acids having 6–22 carbon atoms. Examples of suitable sorbitan derivatives include PEG derivatives of sorbitan wherein the number of repeating ethylene oxide units ranges from 2 to 200, such as PEG sorbitan beeswax, glyceryl/sorbitol/oleate/hydroxystearate, PEG sorbitan cocoate, PEG sorbitan diisostearate, PEG sorbitan isostearate, PEG sorbitan lanolate, PEG sorbitan laurate, PEG sorbitan oleate, PEG sorbitan palmitate, PEG sorbitan perisostearate, PEG sorbitan peroleate, PEG sorbitan stearate, PEG sorbitan tetraoleate, PEG sorbitan tetrastearate, PEG sorbitan triisostearate; Polysorbates such as Polysorbate 20–85, Polysorbtate 80 acetate; and sorbitan esters such as sorbitan caprylate, cocoate, diisostearate, dioleate, distearate, isostearate, laurate, oleate, olivate, palmitate, sesquiisostearate, sesquioleate, sesquistearate, stearate, triisostearate, trioleate and the like. Preferred are Polysorbates, in particular Polysorbate 80.

(c) Glyceryl Ethers

Also suitable are linear or branched ethers of polyglycerol having the general formula:

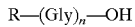

wherein n is 1–10 and R is a straight or branched, saturated or unsaturated alkyl having 6 to 30 carbon atoms, and Gly is the glycerol residue. Examples of suitable polyglyceryl derivatives include polyglyceryl decaoleates, polyglyceryl caprates, polyglyceryl diisostearates, polyglyceryl distearates, polyglyceryl isopalmitates, polyglyceryl laurates, and the like.

(d) Glyceryl Esters

Suitable glyceryl esters include alkoxylated glyceryl esters include synthetic or semi-synthetic glyceryl esters, e.g. fatty acid mono-, di-, and triglycerides which are natural fats or oils that have been modified, for example, by reaction with alkylene oxide units, preferably ethylene oxide units. Examples of such glyceryl esters include PEG glyceryl oleates, PEG glyceryl stearates and isostearates, PEG glyceryl laurates, PEG glyceryl tallowates, and so on. Preferred PEG glyceryl esters include those of the formula:

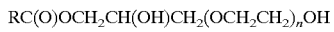

wherein n is 5–200 and RC(O)— is a hydrocarbylcarbonyl group wherein R is preferably an aliphatic radical having 7 to 19 carbon atoms.

Also suitable are glyceryl esters formed by the reaction of glycerol with one or more fatty acids. Examples of these glyceryl esters include glyceryl adipate, caprylate, cocoate, stearate, diisostearate, laurate, linoleate, and so on.

(e) Dialkyl Sulfoxides

Also suitable are long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(f) Polyethylene Oxide Condensates of Alkyl Phenols

Suitable condensates include the condensation products of alkyl phenols having an alkyl group of 6 to 20 carbon atoms with ethylene oxide being present in amounts of about 10 to 60 moles of ethylene oxide per mole of alkyl phenol.

(g) Condensation Products of Ethylene Diamine

Examples of suitable condensation products of ethylene diamine include products of ethylene oxide with the reaction product of propylene oxide and ethylene diamine.

(h) Long Chain Tertiary Amine Oxides

Preferred long chain tertiary amine oxides include those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(i) Long Chain Tertiary Phosphine Oxides

Suitable long chain tertiary phosphine oxides include those corresponding to the general formula:

$$RR_1R_2PO$$

wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(j) Polyhydroxy Fatty Acid Amides

Examples of $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

(k) Alkyl Polysaccharides

Suitable nonionic surfactants are alkyl polysaccharides, or alkyl glycosides, disclosed in U.S. Pat. Nos. 5,716,418 and 5,756,079, both of which are hereby incorporated by reference. These alkylglycosides have the general formula:

$$R_1\text{—}O\text{—}(R_2O)_t\text{—}(G)_n\text{—}H$$

wherein $R_1$ is a linear or branched alkyl or alkenyl radical having 12 to 30 carbon atoms, $R_2$ is a $C_{2-4}$ alkylene, (G) is an anhydroglucose unit, t is a number between 0 and 10, preferably 0 to 4, and n is a number from about 1 to 15. Examples of such alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on. Certain polyglycosides having the above formula are sold by Henkel Corporation under the tradenamnes APG 300, APG 350, APG 500, APG 550, APG 625, or the tradename Planteren, e.g. Planteren 300, 600, 1200, 2000, and so on.

Particularly preferred nonionic surfactants for use in the peroxide compositions are sorbitan derivatives, in particular the Polysorbates.

2. Anionic Surfactants

Also suitable for use as the surface active ingredient are one or more anionic surfactants.

(a) Alkyl Sulfates

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, magnesium, or triethanolamine cation.

Another type of anionic surfactant which may be used in the compositions of the invention are water soluble salts of organic, sulfuric acid reaction products of the general formula:

$$R_1\text{—}SO_3\text{—}M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

(b) Fatty Acids Esterified with Isethionic Acid

Also suitable as anionic surfactants are reaction products of fatty acids esterified with isethionic acid and neutralized with sodium hydroxide. The fatty acids may be derived from coconut oil, for example.

(c) Succinates or Succinimates

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

(d) Olefin Sulfonates

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

(e) N-acyl Amino Acids

Still another class of anionic surfactants include N-acyl amino acid surfactants and salts thereof (alkali, alkaline earth, and ammonium salts) having the formula:

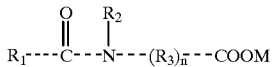

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

The peroxide composition is made by simply combining the ingredients and mixing well with a high speed mixer that will facilitate formation of dispersed aqueous phase microdroplets. The microdroplets will remain in the composition even after it is combined with the aqueous oxidative hair dye composition and applied to the hair. Preferably, the peroxide composition is a clear water in oil microemulsion.

II. THE AQUEOUS ALKALINE COMPOSITION

The aqueous alkaline composition comprises at least one interactive surfactant, and, when mixed with the peroxide composition, is capable of activating the peroxide composition so that it will lighten or color the hair. In addition, the aqueous alkaline composition is compatible with the peroxide composition such that when the two compositions are mixed immediately prior to use, the microdroplets remain in the mixture and are available for deposition onto the hair. Preferably, the aqueous alkaline composition is in the form of an emulsion, which may be water in oil, or oil in water emulsion. When the aqueous alkaline emulsion composition is mixed with the microemulsion peroxide composition the microdroplets remain in the mixture. After mixing, the mixture is applied to the hair and either lightens (bleaches) hair or colors the hair depending on whether the aqueous alkaline composition contains oxidative dye intermediates. The aqueous alkaline composition preferably has a pH of 7.1 to 11, more preferably 7.5 to 9.5, most preferably 7.8 to 9.2. Preferably the aqueous alkaline composition comprises 10–95%, preferably 15–90%, more preferably 15–85% by weight of the total aqueous alkaline composition of water. If the aqueous alkaline composition contains one or more oxidative dye intermediates, when combined with the peroxide composition, the mixture will oxidatively color hair. If the aqueous alkaline composition contains no oxidative dye intermediates, it may simply act as an activator for the peroxide composition upon mixing, and when this mixture is applied to hair it will cause permanent lightening, or bleaching, of the hair. The aqueous alkaline composition preferably comprises one or more of the following ingredients:

A. Interactive Surfactant

The aqueous alkaline composition contains at least one interactive surfactant. The term "interactive surfactant" means any surfactant that is compatible with both the aqueous alkaline composition and the peroxide composition, such that when the peroxide composition and the aqueous alkaline composition are combined immediately prior to use, the microdroplets in the peroxide composition remain in the mixture and are available for deposit and penetration into the hair. Suitable surfactants may be anionic, nonionic, amphoteric, or zwitterionic, provided they are compatible with the amphiphilic surfactant found in the peroxide composition such that when the peroxide composition and the aqueous alkaline compositions are combined immediately prior to use the liquid crystals remain stable in the mixture and are available for deposit and penetration into the hair.

Preferred interactive surfactants include the amphiphilic surfactants mentioned for use in the peroxide composition. In addition, amphoteric, zwitterionic, and cationic surfactants are also suitable provided they fulfill the requirements mentioned herein. Suggested ranges of interactive surfactant are 0.001–20%, preferably 0.01–15%, more preferably 0.05–10% by weight of the total aqueous alkaline composition.

1. Amphoteric Surfactants

Suitable amphoteric surfactants may be imidazolinium compounds having the general formula:

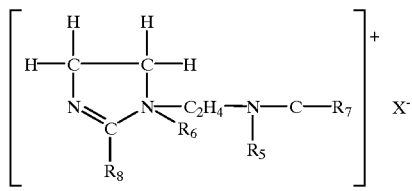

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

Also suitable amphoteric surfactants are monocarboxylates or dicarboxylates such as cocoamphocarboxypropionate, cocoamphocarboxypropionic acid, cocoamphocarboxyglycinate, and cocoamphoacetate.

Other types of amphoteric surfactants include aminoalkanoates of the formula

or iminodialkanoates of the formula:

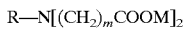

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof 2. Zwitterionic Surfactants Zwitterionic surfactants are also suitable for use in the aqueous alkaline compositions of the invention. The general formula for such surfactants is:

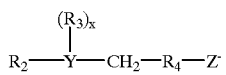

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like.

3. Cationic Surfactants

The aqueous alkaline composition may comprise 0.01–15%, preferably 0.05–10%, preferably 0.10–8% of a cationic surfactant which is, preferably a quaternary ammonium salt or the salt of a fatty amine. Quaternary ammonium salts have the formula:

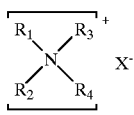

wherein $R_1$ is hydrogen, an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate, hydroxide, and methyl sulfate radicals. The aliphatic groups may contain, in addition to carbon and hydrogen atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, dicetyldimonium chloride, and mixtures thereof Other quaternary ammonium salts useful as the cationic conditioning agent are compounds of the general formula:

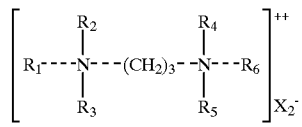

wherein $R_1$ is an aliphatic group having 16 to 22 carbon atoms, $R_2$, $R_3$, $R_4$, $R_5$, and $R_6$ are the same or different and are selected from H and alkyls having 1 to 4 carbon atoms and X is an anion as above defined.

Also suitable are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

B. Oxidative Dye Intermediates

Where the aqueous alkaline composition is in the form of an oxidative dye, the composition will comprise at least one primary intermediate and, optionally, at least one coupler for the formation of oxidation dyes. Examples of suitable oxidative dye intermediates and oxidative dye compositions include those set forth in U.S. Pat. No. 5,143,193, which is hereby incorporated by reference.

1. Primary Intermediates and Couplers

If the aqueous alkaline composition is in the form of an oxidative hair dye composition, the composition contains 0.0001–20%, preferably 0.001–15%, more preferably 0.01–10% (combined weight) of at least one primary intermediate and, optionally, at least one coupler for the formation of oxidation dyes. Preferably, the oxidative dye composition will contain both a primary intermediate and coupler, and if so, the range of primary intermediate will be about 0.0001–5% by weight and the range of coupler will be about 0.0001–5% by weight. Primary intermediates and couplers are well known hair coloring ingredients, and include ortho or para substituted aminophenols or phenylenediamines, such as para-phenylenediamines of the formula:

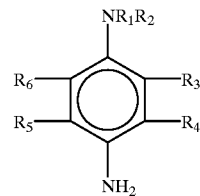

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, phenyl, hydroxy substituted phenyl, alkoxy substituted phenyl, or amino substituted phenyl groups; $R_3$ and $R_6$ are each independently hydrogen, $C_{1-6}$ alkyl, $C_{1-6}$ alkoxy, halogen, or $C_{1-6}$ alkyl substituted with one or more hydroxyl groups; and $R_4$ and $R_5$ are each independently hydrogen, $C_{1-6}$ lower alkoxy, $C_{1-6}$ lower alkyl, or halogen. Examples of suitable primary intermediates are para-aminophenol, para-hydroquinone, ortho-hydroquinone, ortho-phenylenediamines, including para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, and derivatives thereof Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof Suitable couplers include, for example, those having the general formula:

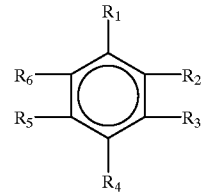

wherein $R_1$ is hydroxy, or amino; or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, halogen, $C_{1-6}$ alkoxy, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, resorcinols, meta-aminophenols, meta-phenylenediamines, and the like, which may be unsubstituted, or substituted on the amino group or benzene ring with alkyl, hydroxyalkyl, alkylamino groups, and the like. Suitable couplers include 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethyloxy-1,3-diaminobenzene, 6-methoxy-5-ethyl-1,3-diaminobenzene, 6-ethyloxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethyloxy)-1,3-diaminobenzene, 6-(beta-hydroxyethyloxy)-1-amino-3-(methylamino)benzene, 6-carboxymethyloxy-1,3-diaminobenzene, 6-ethyloxy-1-bis(beta-hydroxyethyl)amino-3-aminobenzene, 6-hydroxyethyl-1,3-diaminobenzene, 1-hydroxy-2-isopropyl-5-methylaminobenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, and mixtures thereof Preferred couplers include resorcinol, 1-naphthol, 5-amino-o-cresol, resorcinol, 2-methylresorcinol, m-aminophenol, m-phenylenediamine, 1-phenyl-3-methyl-pyrazol-5-one, their salts, or mixtures thereof C. Other Ingredients The aqueous alkaline composition may contain one or more additional ingredients such as those set forth below:

1. Penetration Enhancers

The aqueous alkaline composition may contain one or more penetration enhancers, and if so, suggested ranges are 0.001–20%, preferably 0.01–15%, more preferably 0.1–10% by weight of the total oxidative dye composition is suggested. Suitable penetration enhancers include those mentioned with respect to the peroxide composition.

2. Preservatives

The aqueous alkaline composition may also contain 0.0001–7%, preferably 0.001–5%, more preferably 0.005–3% preservatives. Suitable preservatives include methyl, ethyl, and propyl paraben, DMDM hydantoin, DEDM hydantoin, benzyl alcohol, and the like.

3. Chelating Agents

The aqueous alkaline composition may also contain 0.0001–5%, preferably 0.0005–3%, more preferably 0.001–2% of one or more chelating agents which are capable of complexing with and inactivating metallic ions in order to prevent their adverse effects on the stability or effects of the composition. In particular, the chelating agent in the peroxide will chelate the metal ions found in the water and prevent these ions from interfering with the reaction between the dye molecules and the oxidizing agent. Suitable chelating agents include EDTA and calcium, sodium, or potassium derivatives thereof, HEDTA, sodium citrate, TEA-EDTA, and so on.

4. pH Adjusters

It may also be desireable to add small amounts of acids or bases to adjust the pH of the aqueous alkaline composition to the desired pH range of 7.1 to 11. Suitable acids include hydrochloric acid, phosphoric acid, citric acid, and the like. Suitable bases include sodium hydroxide, potassium hydroxide, and the like.

5. Protein Derivatives

In addition, conditioning agents such as protein derivatives may be added to the aqueous alkaline composition. Generally about 0.001–10%, preferably 0.005–8%, more preferably 0.01–5% by weight of the total composition of protein derivatives is suggested. Examples of protein derivatives are hydrolyzed wheat protein, hydrolyzed wheat protein/wheat oligosaccharides, hydrolyzed marine collagen, wheat amino acids, PVP/hydrolyzed wheat protein copolymer (which is a copolymer of polyvinylpyrrolidone and hydrolyzed wheat protein).

6. Plant Extracts

It may also be desireable to include various plant extracts in the aqueous alkaline composition for extra conditioning and humectancy. Suggested ranges are 0.001–10%, preferably 0.005–8%, more preferably 0.01–5% by weight of the total composition. A preferred plant extract is seaweed extract.

7. Oils

The aqueous alkaline composition may contain one or more oils, and may be in the form of a water in oil or oil in water emulsion. Suggested ranges of oil are 0.1–40%, preferably 0.5–30%, more preferably 1–25% by weight of the total oxidative dye composition. Suitable oils are the esters and other oils mentioned for use in the peroxide composition.

8. Cationic Conditioning Polymers

The aqueous alkaline composition may contain one or more cationic conditioning polymers. Suggested ranges are 0.01–20%, preferably 0.05–15%, more preferably 0.1–10% by weight of the total aqueous alkaline composition. Examples of cationic conditioning polymers include:

(a) Quaternary derivatives of cellulose ethers such as polymers sold under the tradename JR-125, JR-400, JR-30M. Preferred is Polyquaternium 10, which is a polymeric quaternary ammonium salt of hydroxyethyl cellulose reacted with a trimethyl ammonium substituted epoxide.

(b) Copolymers of vinylpyrrolidone having monomer units of the formula:

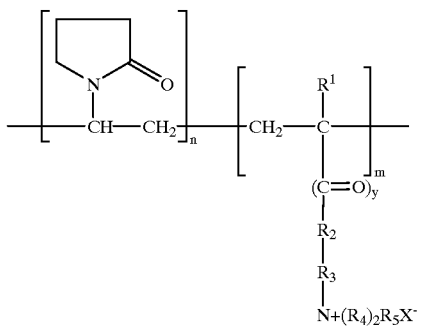

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—(CHOH—($CH_2$—), preferably $C_xH_{2x}$ where x is 2;

$R^4$ is methyl, ethyl, phenyl, preferably methyl; and $R^5$ is methyl, ethyl, phenyl, or $C_{1-4}$ substituted phenyl; preferably methyl.

Preferred are compounds of the above formula wherein y is 1, $R^2$ is NH, $R^3$ is $CH_2CH_2$, $R^4$ is methyl, and $R^5$ is methyl. Such compounds are known by the CTFA designation Polyquaternium 28.

(c) Homopolymer of dimethyldiallylammonium chloride, or copolymer of dimethyldiallylammonium chloride and acrylamide. Such compounds are sold under the tradename MERQUAT™ by Merck.

(d) Homopolymers or copolymers derived from acrylic methacrylic acid wherein the monomer units are selected from the group consisting of acrylamide, methylacrylamide, diacetone-acrylamide, acrylamide or methacrylamide substituted on the nitrogen by lower alkyl, alkyl esters of acrylic acid and methacrylic acid, vinylpyrrolidone, and vinyl esters.

Examples of cationic polymers that can be used in the compositions of the invention are the cationic polymers disclosed in U.S. Pat. Nos. 5,240,450 and 5,573,709, which are hereby incorporated by reference.

Preferred aqueous alkaline compositions for oxidative dyeing of hair comprise:

0.0001–20% (combined weight) of at least one primary intermediate and, optionally, at least one coupler for the formation of oxidation dyes, 0.001–20% of an interactive surfactant, 10–95% water.

Preferred aqueous alkaline compositions for bleaching of hair comprise:

0.001–20% of an interactive surfactant,

10–95% water, and 0.001–20% humectant.

If desired, both compositions may contain one or more of the ingredients mentioned above.

III. THE METHOD

The invention comprises a method for oxidative dyeing of hair comprising the steps of:

(a) combining, immediately prior to use,
  (1) an aqueous oxidative dye composition comprising at least one primary intermediate and, optionally, at least one coupler for the formation of oxidation dyes and an interactive surfactant; and
  (2) a water in oil microemulsion peroxide composition comprising, by weight of the total composition:
    (i) 1–99% of an aqueous phase in the form of dispersed microdroplets having a droplet size of 100 to 1500 Angstroms,
    (ii) 0.1–75% of a continuous oil phase; and
    (iii) 1–65% of an organic, surface active ingredient capable of interacting with the water phase and the oil phase to cause formation of the dispersed aqueous phase microdroplets, all percentages by weight of the total composition; and (b) applying said mixture of (1) and (2) to the hair for an amount of time, preferably 5 to 10 minutes, to cause permanent coloration of hair.

In the method of the invention, about 1 to 5 parts of the peroxide composition is mixed with about 1 to 5 parts of the oxidative dye composition immediately prior to application on the hair. The mixture is applied to the hair and allowed to remain for the desired time period, which is preferably 5 to 10 minutes. If desired, the mixture can be left on the hair longer if, for example, the hair is very resistant to dye. Thereafter, the mixture is rinsed from the hair with water until clean. If desired, a hair conditioner may be applied to the hair.

The invention also comprises a method for bleaching hair comprising the steps of:

(a) combining, immediately prior to use,
  (1) an aqueous alkaline compostion comprising at least one interactive surfactant; and
  (2) a water in oil microemulsion peroxide composition comprising, by weight of the total composition:
    (i) 1–99% of an aqueous phase in the form of dispersed microdroplets having a droplet size of 100 to 1500 Angstroms,
    (ii) 0.1–75% of a continuous oil phase; and
    (iii) 1–65% of an organic, surface active ingredient capable of interacting with the water phase and the oil phase to cause formation of the dispersed aqueous phase microdroplets, all percentages by weight of the total composition; and (b) applying said mixture of (1) and (2) to the hair for an amount of time, preferably 5 to 10 minutes, to cause lightening or bleaching of the hair.

In the bleaching method of the invention, about 1 to 5 parts of the peroxide composition is mixed with about 1 to 5 parts of the aqueous alkaline composition immediately prior to application on the hair. The mixture is applied to the hair and allowed to remain for the desired time period, which is preferably 5 to 10 minutes. If desired, the mixture can be left on the hair longer if, for example, the hair is very resistant to bleach. Thereafter, the mixture is rinsed from the hair with water until clean. If desired, a hair conditioner may be applied to the hair.

The invention further comprises a method for reducing the amount of time required to permanently color hair, comprising treating the hair with a mixture of a microemulsion peroxide composition and an aqueous alkaline composition containing at least one interactive surfactant.

The presence of the microdroplets in the microemulsion containing the active ingredients, e.g. the hydrogen peroxide, causes increased penetration of the oxidizing agent into the hair shaft, and thereby decreasing the amount of time necessary to achieve full coloration or lightening of the hair.

The compositions and methods of the invention provide permanent coloration or lightening of hair in as little as five to ten minutes. The coloring or lightening is permanent, which means that it lasts from about four to eight weeks.

The invention will be further described in connection with the following examples, which are set forth for the purposes of illustration only.

EXAMPLE 1

Peroxide compositions in the water in oil microemulsion form were prepared according to the following formula:

| | w/w % | |
|---|---|---|
| | 1 | 2 |
| Water | 12.00 | 7.00 |
| Hydrogen peroxide (35% aqueous solution) | 18.00 | 18.00 |
| Tween 80* | 35.00 | — |
| Sodium lauryl sulfate | — | 20.00 |
| Isopropyl myristate | 15.00 | — |

-continued

|  | w/w % | |
|---|---|---|
|  | 1 | 2 |
| Polydecene | — | 15.00 |
| Pentanol | — | 40.00 |
| Benzyl alcohol | 20.00 | — |

*Polysorbate 80: oleate esters of sorbitol and sorbitol anhydrides condensed with about 20 moles of ethylene oxide.

The compositions were made by combining the ingredients and mixing well to form a water in oil microemulsion having dispersed microdroplets, wherein the droplets had a size of about 100 to 700 Angstroms.

EXAMPLE 2

Water in oil microemulsion peroxide compositions were made as follows:

|  | w/w % | | | | |
|---|---|---|---|---|---|
|  | 1 | 2 | 3 | 4 | 5 |
| Water | 12.00 | 12.00 | 12.00 | 12.00 | 12.00 |
| Hydrogen Peroxide* | 18.00 | 18.00 | 18.00 | 18.00 | 18.00 |
| Tween 80 | 30.00 | 40.00 | 30.00 | 15.00 | 20.00 |
| Isopropyl myristate | 20.00 | 20.00 | 20.00 | 25.00 | 20.00 |
| Benzyl alcohol | 15.00 | 10.00 | 20.00 | 15.00 | 10.00 |
| Ethoxy diglycol | 5.00 | — | — | — | — |
| Oleth-10 | — | — | — | 15.00 | — |
| Labrasol** | — | — | — | — | 20.00 |

*35% aqueous solution
**Polyoxyethylene (8) caprylic/capric glycerides

The compositions were made by combining the ingredients and mixing well to form a water in oil microemulsion having dispersed aqueous phase microdroplets, wherein the droplets had a size of about 100 to 700 Angstroms.

EXAMPLE 3

A composition for oxidative dyeing of hair was made as follows:

|  | w/w % |
|---|---|
| Ammonium lauryl sulfate (anionic surfactant) | 2.00 |
| Propylene glycol (humectant) | 4.00 |
| Ethoxydiglycol (solvent) | 2.00 |
| Monoethanolamine (pH adjuster) | 5.00 |
| Seaweed extract (conditioner) | 0.80 |
| EDTA (chelating agent) | 0.80 |
| Isoascorbic acid (antioxidant) | 0.20 |
| Sodium sulfite (reducing agent) | 0.50 |
| Primary intermediates and couplers (dye) | 5.00 |
| Oleic acid (soap) | 12.50 |
| Cetearyl alcohol (opacifier) | 4.00 |
| Emulsifying wax (emulsifier) | 2.00 |
| Oleth-20 (nonionic surfactant) | 1.00 |
| Steareth-21 (nonionic surfactant) | 0.70 |
| Meadowfoam seed oil (oil) | 0.75 |
| Oleyl alcohol (oil) | 0.40 |
| Polyquaternium 10 (cationic surfactant) | 0.20 |
| Polyquaternium 28 (cationic surfactant) | 0.50 |
| Mica/titanium dioxide (colorant) | 0.30 |
| Hydrolyzed wheat protein (conditioner) | 1.00 |
| Cibafast W liquid* (UV absorber) | 1.00 |
| Fragrance | 0.75 |
| Ammonium hydroxide (pH adjuster) | 5.00 |
| Wheat amino acids (conditioner) | 1.00 |
| Water | QS |

*sodium isobutyl benzotriazole sulfonate, Ciba Geigy

The composition was made by first dissolving the first eight ingredients in water. The primary intermediates and couplers were then added with heat to dissolve. The remaining ingredients, except for the ammonium hydroxide, wheat amino acids, and fragrance were mixed separately and added after the primary intermediates and couplers. The remaining water, ammonium hydroxide, hydrolyzed wheat protein, wheat amino acids, and fragrance were finally added to the mixture.

EXAMPLE 4

About 1.5 parts of the peroxide composition of Example 2 was mixed with 1 part of the oxidative hair dye composition of Example 3 and applied to natural light brown hair. The composition was left on the hair for five minutes, and then rinsed out with water. The resulting hair was lightened several shades.

EXAMPLE 5

An aqueous alkaline composition suitable for mixing with the peroxide composition to form a hair bleach was prepared as follows:

|  | w/w % |
|---|---|
| Erythrobic acid | 0.20 |
| Sodium sulfite | 0.50 |
| Propylene glycol | 4.00 |
| Ethoxydiglycol | 2.00 |
| Tetrasodium EDTA (38% aqueous Solution) | 0.80 |
| Ethanolamine | 5.00 |
| Hypnea musciformis extract/gellidiela acerosa/extract, sargassum filipendula extract/sorbitol | 0.80 |
| Sodium benzotriazole sulfonate/buteth-3/propane tricarboxylic acid | 1.00 |
| Ammonium lauryl sulfate (28% aqueous solution) | 2.00 |
| Oleic acid | 12.50 |
| Cetearyl alcohol | 4.00 |
| Emulsifying wax | 2.00 |
| Oleth-20 | 1.00 |
| Steareth-21 | 0.70 |
| Meadowfoam seed oil | 0.75 |
| Oleyl alcohol | 0.40 |
| Polyquaternium-10 | 0.20 |
| Polyquaternium-28 | 0.50 |
| Mica/titanium dioxide (67:33) | 0.30 |
| Hydrolyzed wheat protein | 1.00 |
| Wheat amino acids | 1.00 |
| Fragrance | 0.75 |
| Ammonium hydroxide (27.5% aqueous solution) | 5.00 |
| Water | QS |

The composition was prepared by combining all of the ingredients and mixing well.

EXAMPLE 6

About 1.5 parts of the peroxide composition of Example 2 was mixed with 1 part of the aqueous alkaline composition of Example 5 and applied to brown hair. The composition was left on the hair for 5 to 10 minutes, then rinsed out with water. The lightening obtained on the hair was equivalent to the lift obtained with a standard bleach composition after 45 minutes.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A water in oil microemulsion peroxide composition for coloring or lightening hair comprising:
    (a) 1–99% of an aqueous phase in the form of dispersed microdroplets having a droplet size of 100 to 1500 Angstroms, said aqueous phase containing hydrogen peroxide,
    (b) 0.1–75% of a continuous oil phase; and
    (c) 1–65% of an organic, surface active ingredient capable of interacting with the water phase and the oil phase to cause formation of the dispersed aqueous phase microdroplets containing hydrogen peroxide, all percentages by weight of the total composition.

2. The composition of claim 1 wherein the oil phase comprises a volatile oil, a nonvolatile oil, or mixtures thereof.

3. The composition of claim 2 wherein the oil phase comprises a nonvolatile organic oil.

4. The composition of claim 3 wherein the nonvolatile oil comprises an organic oil which is an ester, hydrocarbon, fatty alcohol, lanolin, or mixtures thereof.

5. The composition of claim 4 wherein the nonvolatile oil comprises an ester of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl.

6. The composition of claim 5 wherein the nonvolatile oil is selected from the group consisting of isopropyl myristate, isotridecyl isononanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and mixtures thereof.

7. The composition of claim 4 wherein the nonvolatile oil is a hydrocarbon.

8. The composition of claim 1 wherein the organic surface active ingredient is a nonionic, anionic, amphoteric, zwitterionic, or cationic surfactant, or mixtures thereof.

9. The composition of claim 1 wherein the organic surface active ingredient comprises a nonionic or anionic surfactant, or mixtures thereof.

10. The composition of claim 9 wherein the nonionic surfactant has an HLB of 12 to 16.

11. The composition of claim 10 wherein the nonionic surfactant is an alkoxylated alcohol, sorbitan derivative, glyceryl ether, glyceryl ester, alkyl polysaccharde, or mixtures thereof.

12. The composition of claim 11 wherein the nonionic surfactant is a sorbitan derivative.

13. The composition of claim 12 wherein the sorbitan derivative is a Polysorbate.

14. The composition of claim 9 wherein the anionic surfactant is an alkyl sulfate or alkyl ether sulfate.

15. A method for coloring or lightening hair comprising the steps of:
    (a) combining, immediately prior to use,
        (1) an aqueous alkaline composition comprising at least one interactive surfactant; and
        (2) a water-in-oil emulsion peroxide composition for coloring or lightening hair comprising, by weight of the total composition:
            (a) 1–99% of an aqueous phase in the form of dispersed microdroplets having a droplet size of 100 to 1500 Angstroms, said aqueous phase containing hydrogen peroxide;
            (b) 0.1–75% of a continuous oil phase; and
            (c) 1–65% of an organic, surface active ingredient capable of interacting with the water phase and the oil phase to cause formation of the dispersed aqueous phase microdroplets, all percentages by weight of the total composition.

16. The method of claim 15 wherein the mixture is left on the hair for five to ten minutes.

17. The method of claim 15 wherein the aqueous alkaline composition is an oxidative dye composition further comprising at least one primary intermediate for the formation of oxidation dyes.

18. The method of claim 17 wherein the oxidative dye composition contains 0.001–5% by weight of the total composition of at least one primary intermediate and at least one coupler for the formation of oxidation dyes.

19. The method of claim 15 wherein the mixture of the aqueous alkaline composition and the peroxide composition forms a composition which bleaches the hair.

20. A method for reducing the amount of time required to permanently color hair, comprising treating the hair with a water in oil microemulsion peroxide composition comprising:
    (a) 1–99% of an aqueous phase in the form of dispersed microdroplets having a droplet size of 100 to 1500 Angstroms, said aqueous phase containing hydrogen peroxide,
    (b) 0.1–75% of a continuous oil phase; and
    (c) 1–65% of an organic, surface active ingredient capable of interacting with the water phase and the oil phase to cause formation of the dispersed aqueous phase microdroplets containing hydrogen peroxide, all percentages by weight of the total composition.

* * * * *